US009821029B2

(12) United States Patent
Cook et al.

(10) Patent No.: US 9,821,029 B2
(45) Date of Patent: Nov. 21, 2017

(54) METHODS OF REDUCING *SALMONELLA* IN POULTRY (71) Applicants: WISCONSIN ALUMNI RESEARCH FOUNDATION, Madison, WI (US); The United States of America as Represented by the Secretary of Agriculture, Washington, DC (US)

(72) Inventors: Mark Eric Cook, Madison, WI (US); Jordan Marshall Sand, Madison, WI (US); Mike H. Kogut, College Station, TX (US); Christina L. Swaggerty, College Station, TX (US)

(73) Assignees: WISCONSIN ALUMNI RESEARCH FOUNDATION, Madison, WI (US); THE UNITED STATES OF AMERICA AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 10 days.

(21) Appl. No.: 14/801,160

(22) Filed: Jul. 16, 2015

(65) Prior Publication Data
US 2015/0313964 A1 Nov. 5, 2015

Related U.S. Application Data (62) Division of application No. 13/957,601, filed on Aug. 2, 2013, now abandoned.

(51) Int. Cl.
*A61K 38/20* (2006.01)
*A23K 1/18* (2006.01)
*A23K 1/17* (2006.01)
*C07K 16/24* (2006.01)
*A61K 39/395* (2006.01)
*A23K 20/147* (2016.01)
*A23K 20/195* (2016.01)
*A23K 50/75* (2016.01)
*A61K 39/00* (2006.01)

(52) U.S. Cl.
CPC ........ *A61K 38/2066* (2013.01); *A23K 20/147* (2016.05); *A23K 20/195* (2016.05); *A23K 50/75* (2016.05); *A61K 39/3955* (2013.01); *C07K 16/244* (2013.01); *A61K 2039/505* (2013.01); *A61K 2039/542* (2013.01); *A61K 2039/545* (2013.01); *C07K 2317/10* (2013.01); *C07K 2317/11* (2013.01)

(58) Field of Classification Search
None
See application file for complete search history.

(56) References Cited

U.S. PATENT DOCUMENTS

| 5,102,872 A | 4/1992 | Singh et al. |
| 5,741,489 A | 4/1998 | Pimentel |
| 5,989,867 A | 11/1999 | Knappe et al. |
| 6,608,172 B1 | 8/2003 | Chiou |
| 8,652,457 B2 | 2/2014 | Sand et al. |
| 2006/0228448 A1 | 10/2006 | Bolleau et al. |
| 2009/0022691 A1 | 1/2009 | Moore et al. |
| 2009/0186038 A1 | 7/2009 | Reed |
| 2013/0109619 A1 | 5/2013 | Tarasova et al. |
| 2014/0017248 A1 | 1/2014 | Sand et al. |
| 2014/0127220 A1 | 5/2014 | Sand et al. |
| 2015/0037277 A1 | 2/2015 | Cook et al. |
| 2016/0280778 A1 | 9/2016 | Cook et al. |

FOREIGN PATENT DOCUMENTS

| WO | 9404174 A1 | 3/1994 |
| WO | 9506657 A1 | 3/1995 |
| WO | 2008086621 A1 | 7/2008 |
| WO | 2015017132 A1 | 2/2015 |

OTHER PUBLICATIONS

Erova et al (Front Cell Infect Microbiol. Nov. 10, 2016;6:148).*
Salazar et al, Front. Immunol. Conference Abstract: IMMUNOCOLOMBIA2015 at the 11th Congress of the Latin American Association of Immunology, 2015.*
Bai et al (PLoS Pathog 5(10):Oct. 2009).*
Vajdos et al. (J Mol Biol. Jul. 5, 2002;320(2):415-28 at 416).*
Brown et al. (J Immunol. May 1996;156(9):3285-91.*
Cruse et al., Illustrated Dict. of Immunology, 2nd ed., CRC Press, 2003, p. 46.*
Bork, Peer; "Power and Pitfalls in Sequence Analysis: The 70% Hurdle"; Genome Research; 10; pp. 398-400; (2000).
Bowie et al.; "Deciphering the Message in Protein Sequences: Tolerance to Amino Acid Substitutions"; Science; 247 (4948); pp. 1306-1310; (1990).
Brown et al.; Tolerance to Single, but Not Multiple, Amino Acid Replacements in Antibody Vh CFR2; J. Immunol.; 156; pp. 3285-3291; (1996).
Burgess, et al.; "Possible Dissociation of the Heparin-binding and Mitogenic Activities of Heparin-binding(Acidic Fibroblast)Growth Factor-1 from Its Receptor-inding Activities by Site-directed Mutagenesis of a Single Lysine Residue"; J.Cell. Biol. 111; pp. pp. 2129-2138 (1990).

(Continued)

*Primary Examiner* — Brian J Gangle
*Assistant Examiner* — Andrea McCollum
(74) *Attorney, Agent, or Firm* — Cantor Colburn LLP (57) ABSTRACT Described herein are methods of reducing *Salmonella* in the intestines of poultry in need thereof by administering to a poultry bird an effective amount of an interleukin-10 peptide or an isolated antibody that specifically binds an interleukin-10 peptide. Administering may be performed within 1 to 4 weeks of harvest of the poultry in order to reduce *Salmonella* transmission to human consumers. Also included herein are finishing feeds that include an interleukin-10 peptide or an isolated antibody that specifically binds an interleukin-10 peptide.

12 Claims, 3 Drawing Sheets

(56) References Cited

OTHER PUBLICATIONS

Hodek et al.; "Chicken Antibodies—Superior Alternative for Conventional Immunoglobulins"; Proc. Indian Sci Acad; B69(4); pp. 461-468; (2003).
Vajdos, et al.; Comprehensive Functional Maps of the Antigen-binding Site of an Anti-ErbB2 Antibody Obtained with Shotgun Scanning Mutagenesis; J. Mol. Biol. 320; pp. 415-428; (2002).
Lazar et al.; "Transforming Growth Factor a: Mutation of Aspartic Acid 47 and Leucine 48 Results in Different Biological Activities"; Molecular and Cellular Biology; pp. 1247-1252; (1988).
den Hartog et al.; "Modulation of Human Immune Responses by Bovine Interleukin-10"; PLoS ONE; 6(3); pp. 1-10; (2011).
"Anthelmintic Resistance: An Examination of its Growing Prevalence in the U.S. Cattle Herd", Executive Summary of the 2005 Anthelmintic ResistanceRoundtable; http://www.merck-animal-health-usa.com/binaries/Anthel_Resist_Exec_Summary_2_tcm96-86774.pdf; 8.
Alam et al.; "A2A Adenosine Receptor (AR) Activation Inhibits Pro-inflammatory Cytokine Production by Human CD4+ Helper T Cells and Regulates Helicobacter-induced Gastritis and Bacterial Persistence"; Mucosal Immunology; 2(3); pp. 232-242; (2009).
Arai et al.; "Effects of In Vivo Adminsitration of Anti-IL-10 Monoclonal Antibody on the Host Defence Mechanism Against Murine *Salmonella* Infection"; Immunology; pp. 381-388; (1995).
Barnes et al.; "Selection of Different Genotype Larvae and Adult Worms for Anthelmintic Resistance by Persistent and Short-Acting Avermectin/Milbemycins"; International Journal for Parasitology; 31; pp. 720-727; (2001).
Campbell et al.; "Susceptability to *Cryptosporidium parvum* Infections in Cytokine—and Chemokine-Receptor Knockout Mice"; Journal of Parasitology; 88(5); pp. 1014-1016; (2002).
Canals, et al.; "Cytokine Profile Induced by a Primary Infection with Ostertagia Ostertagi in Catdtle"; Veterinary Immunology and Immunopathology; 58; pp. 63-75; (1997).
Chen et al; "Oral Administration of a Combination of Select Lactic Acid Bacteria Strains to Reduce the *Salmonella* Invasion and Inflammation of Broiler Chicks"; Poultry Science; 91(9); pp. 2139-2147; (2012).
Coles et al.; "The Detection of Anthelmintic Resistance in Nematodes of Veterinary Importance"; Veterinary Parasitology; 136; pp. 167-185; (2006).
Collier et al.; "Coccidia-induced Mucogenesis Promotes the Onset of Necrotic Enteritis by Supporting Clostridium Perfringens Growth"; Veterinary Immunology and Immunopathology; 112; pp. 104-115; (2008).
Cook, M. E.; "Triennial Growth Symposium: A Review of Science Leading to Host-Targeted Antibody Strategies for Preventing Growth Depression Due to Microbial Colonization"; J. Animal Sci; 89; pp. 1981-1990; (2011).
Co-pending U.S. Appl. No. 13/548,840, filed Jul. 16, 2012; Interleukin-10 Peptides and Antibodies Thereof for Inhibiting Adverse Effects of Protozoan Infection; 25 pages.
De Meulenaer et al.; "Isolation and Purification of Chicken Egg Yolk Immunoglobulins: A Review"; Food and Agricultural Immunology; 13(4); pp. 275-288; (2001).
Filho et al.; "Humoral and Cellular Immune Response Generated by Different Vaccine Programs Before and After *Salmonella enteritidis* Challenge in Chickens"; Vaccine; 30; pp. 7637-7643; (2012).
Ghebremicael et al.; "Association of Interleukin-10 Cluster Genes and *Salmonella* Response in the Chicken"; Poultry Science; 87(1); pp. 22-26; (2008).

International Search Report and Written Opinion; International Application No. PCT/US2014/047002; International Fling Date Jul. 17, 2014; dated Dec. 12, 2014; 14 pages.
Lee et al.; "IL-10 Suppresses Bactericidal Response of Macrophages Against *Salmonella typhimurium*"; Journal of Microbiology; 49(6); pp. 1050-1053; (2011).
Li, Robert W. et al.; "Localized Complement Activation in the Development of Protective Immunity Against Ostertagia Ostertagi Infections in Cattle"; Veterinary Parasitology; 174; pp. 247-256; (2010).
Li, Robert W., et al.; "Local Inflammation as a Possible Mechanism of Resistance to Gastrointestinal Nematodes in Angus Heifers"; Veterinary Parasitology; 145; pp. 100-107p (2007).
Yazwinski et al.; "Fecal Egg Count Reduction and Control Trial Determinations of Anthelmintic Efficacies for Several Parasiticides Utilizing a Single Set of Naturally Infected Calves"; Veterinary Parasitology; 164; pp. 232-241; (2009).
Rothwell et al.; "Cloning and Characterization of Chicken IL-10 and Its Role in the Immune Response to Eimeria maxima"; Journal of Immunology; 173; pp. 2675-2682; (2004).
Sand et al. "Oral Antibody to Interleukin-10 Prevents Growth Suppression by Coccidia Infection"; from Poultry Science Association 101st Annual Meeting Abstracts; Abstract P310; Jul. 9-12, 2012; Poult.Sci. 91(supp.1) p. 107.
Setta et al.; "Early immune dynamics following Infection with *Salmonella enterica* serovars Enteridis, Infantis, Pullorum and Gallinarum: Cytokine and chemokine gene expression profile and cellulsr changes of chicken ceca tonsils"; Comparative Immunology.
Symonds et al.; "Bifidobacterium Infantis 35624 Protects Against *Salmonella*-Induced Reductions in Digestive Enzyme Activity in Mice by Attenuation of the Host Inflammatory Response"; Clinical and Translational Gastroenterology; 3, e15; doi:10.1038/ctg.2.
Wei et al.; "*Salmonella enterica* Serovar Typhi Plasmid Impairs Dendritic Cell Responses to Infection"; Curr Microbiol; 65; pp. 133-140; (2012).
Williams, R.B.; "Anticcoccidial Vaccines for Broiler Chickens: Pathways to Success"; Avian Pathology; 31(4); pp. 317-353; (2002).
Alba-Hurtado et al.; "Immune Responses Associated with Resistance to Haemonchosis in Sheep"; BioMed Research International; 2013, Article ID 162158; 11 pages; (2013).
Aly et al.; "Agreement Between Bovine Respiratory Disease Scoring Systems for Pre-weaned Dairy Calves"; Animal Health Research Reviews; 15(2); pp. 148-150; (2014).
Bobeck et al.; "Oral Peptide Specific Egg Antibody to Intestinal Sodium-dependent Phosphate Co-transporter-2b is Effective at Altering Phosphate Transport in Vitro and in Vivo", Poultry Science; 94; pp. 1128-1137; (2015).
Fawzi et al.; "Intranasal Immunization of Lambs with Serine/Threonine Phosphatase 2A Against Gastrointestinal Nematodes"; Clinical and Vaccine Immunology; 20:9; pp. 1352-1359; (2013).
Greenspan et al.; "Defining Epitopes: It's Not As Easy as It Seems"; Nature Biotechnology; 7; pp. 936-937; (1999).
MacCallum et al.; "Antibody-antigen Interactions: Contact Analysis and Binding Site Topography"; J. Mol. Biol. 262; pp. 732-745; (1996).
Nuflor; "Bovine Respiratory Diseases: A New Look at Causes and Signs of Disease"; found in MERCK Animal Health ; http://www.nuflor.com/diseases/brd-nlac.asp; 4 pages; printed Mar. 3, 2017.
Paul, Fundamental Immunology, Third Edition (textbook), "Fv Structure and Diversity in Three Dimensions" pp. 292-295; Raven Press, New York (1993).

* cited by examiner

```
                         SEQUENCE LISTING

<160> NUMBER OF SEQ ID NOS: 20

<210> SEQ ID NO 1
<211> LENGTH: 8
<212> TYPE: PRT
<213> ORGANISM: Gallus gallus

<400> SEQUENCE: 1

Asp Asp Glu Leu Asn Ile Gln Leu
1               5

<210> SEQ ID NO 2
<211> LENGTH: 8
<212> TYPE: PRT
<213> ORGANISM: Gallus gallus

<400> SEQUENCE: 2

Val Leu Pro Arg Ala Met Gln Thr
1               5

<210> SEQ ID NO 3
<211> LENGTH: 8
<212> TYPE: PRT
<213> ORGANISM: Meleagris gallopavo

<400> SEQUENCE: 3

Val Leu Pro Arg Ala Met Lys Thr
1               5

<210> SEQ ID NO 4
<211> LENGTH: 8
<212> TYPE: PRT
<213> ORGANISM: Gallus gallus

<400> SEQUENCE: 4

Glu Lys Met Asp Glu Asn Gly Ile
1               5

<210> SEQ ID NO 5
<211> LENGTH: 8
<212> TYPE: PRT
<213> ORGANISM: Gallus gallus

<400> SEQUENCE: 5
```

Glu Pro Thr Cys Leu His Phe Ser
1               5

<210> SEQ ID NO 6
<211> LENGTH: 7
<212> TYPE: PRT
<213> ORGANISM: Sus scrofa

<400> SEQUENCE: 6

Asp Gln Met Gly Asp Leu Leu
1               5

<210> SEQ ID NO 7
<211> LENGTH: 7
<212> TYPE: PRT
<213> ORGANISM: Bos taurus

<400> SEQUENCE: 7

Asp Gln Leu His Ser Leu Leu
1               5

<210> SEQ ID NO 8
<211> LENGTH: 8
<212> TYPE: PRT
<213> ORGANISM: Sus scrofa

<400> SEQUENCE: 8

Val Met Pro Lys Ala Glu Ser Asp
1               5

<210> SEQ ID NO 9
<211> LENGTH: 8
<212> TYPE: PRT
<213> ORGANISM: Bos taurus

<400> SEQUENCE: 9

Val Met Pro Gln Ala Glu Asn His
1               5

<210> SEQ ID NO 10
<211> LENGTH: 8
<212> TYPE: PRT
<213> ORGANISM: Sus scrofa

<400> SEQUENCE: 10

Ser Lys Leu Gln Glu Arg Gly Val
1               5

<210> SEQ ID NO 11
<211> LENGTH: 8
<212> TYPE: PRT
<213> ORGANISM: Bos taurus

<400> SEQUENCE: 11

Ser Glu Leu Gln Glu Arg Gly Val
1               5

<210> SEQ ID NO 12
<211> LENGTH: 8
<212> TYPE: PRT
<213> ORGANISM: Sus scrofa

<400> SEQUENCE: 12

Glu Asn Ser Cys Ile His Phe Pro

```
<210> SEQ ID NO 13
<211> LENGTH: 8
<212> TYPE: PRT
<213> ORGANISM: Bos taurus

<400> SEQUENCE: 13

Asp Ser Ser Cys Ile His Leu Pro
1               5

<210> SEQ ID NO 14
<211> LENGTH: 7
<212> TYPE: PRT
<213> ORGANISM: Ovis aries

<400> SEQUENCE: 14

Asp Gln Leu Asn Ser Met Leu
1               5

<210> SEQ ID NO 15
<211> LENGTH: 8
<212> TYPE: PRT
<213> ORGANISM: Ovis aries

<400> SEQUENCE: 15

Asn Met Leu Gln Glu Arg Gly Val
1               5

<210> SEQ ID NO 16
<211> LENGTH: 8
<212> TYPE: PRT
<213> ORGANISM: Ovis aries

<400> SEQUENCE: 16

Asp Ser Ser Cys Thr His Phe Pro
1               5

<210> SEQ ID NO 17
<211> LENGTH: 7
<212> TYPE: PRT
<213> ORGANISM: Gadus morhua

<400> SEQUENCE: 17

Asp Asp Leu Glu Ile Gly Leu
1               5

<210> SEQ ID NO 18
<211> LENGTH: 12
<212> TYPE: PRT
<213> ORGANISM: Gadus morhua

<400> SEQUENCE: 18

Val Leu Pro Thr Ala Ile Ala Asp Met Thr Glu Glu
1               5                   10

<210> SEQ ID NO 19
<211> LENGTH: 8
<212> TYPE: PRT
<213> ORGANISM: Gadus morhua

<400> SEQUENCE: 19

Thr Gln Met Glu Gly Lys Gly Pro
1               5
```

```
<210> SEQ ID NO 20
<211> LENGTH: 7
<212> TYPE: PRT
<213> ORGANISM: Gadus morhua

<400> SEQUENCE: 20

Asn Gln Cys Cys Arg Phe Val
1               5
```

METHODS OF REDUCING *SALMONELLA* IN POULTRY

CROSS-REFERENCE TO RELATED APPLICATIONS

This application is a divisional of U.S. application Ser. No. 13/957,601 filed on Aug. 2, 2013, which is incorporated herein by reference in its entirety.

FIELD OF THE DISCLOSURE

The present disclosure is related to methods of reducing *Salmonella* in the intestines of animals, including poultry.

BACKGROUND

Livestock such as poultry that are infected with pathogens, or serve as incubatory or convalescent carriers of pathogens, present problems both for the animals as well as humans who consume meat from the animals. Antibiotics are generally added to the nursery and grower feeds of poultry to promote growth and/or reduce disease occurrence during all phases of food production. The addition of antibiotics reduces the passage of pathogens such as *S. Enteritidis* to humans and has advantages for the health and weight of the poultry. Antibiotics promote growth through the reduction of biological stress, the decrease of bacteria, and by promoting the health of the poultry. Poultry that are healthy and disease free eat more food, and more effectively convert the food into muscle or meat. Thus, the antibiotic supplementation of poultry diet has numerous benefits.

Despite the advantages, the practice of supplementing poultry diet with antibiotics is increasingly problematic. Sub-therapeutic doses of antibiotics are linked to the increased presence of antibiotic-resistant bacterial strains in humans, animals and in the environment. It is also possible for residual antibiotics to appear in food that is meant for human consumption. To prevent residues, antibiotics are generally withdrawn from the feed of the poultry at least two weeks prior to slaughter to allow for drug clearance, and hence to prevent the antibiotics sequestered in the poultry from ingestion by humans.

Of particular importance to human consumers is Salmonellosis (*Salmonella* infection), associated with the pathogen *Salmonella enterica* subspecies *enterica* serovar Enteritidis (*S. Enteritidis*). Poultry products, including eggs and poultry birds, serve as a reservoir for *S. Enteritidis*. Poultry birds can be asymptomatic for *Salmonella* infection, thus making it difficult to isolate infected birds. The *S. Enteritidis* pathogen can pass to humans via contaminated poultry products through the food production chain. Undercooked or raw eggs and poultry meat thus constitute a high risk of infection for humans. In fact, poultry carcasses entering the processing environment are generally contaminated with bacteria such as *Salmonella*.

As one example of an attempt to prevent the transmission of *Salmonella* to human consumers, ground turkey samples are routinely tested for *Salmonella*. For example, 25 gram samples of ground turkey are tested and 50% of the samples must be free of *Salmonella*. Recent outbreaks of food poisoning associated with ground turkey have prompted proposals to increase the standards for ground turkey, which with current production methods may greatly increase the number of samples testing positive for *Salmonella*. What is needed are improved antibiotic-free methods of treating poultry to reduce the incidence of *Salmonella* in poultry products.

BRIEF SUMMARY

In one aspect, a method of reducing *Salmonella* in the intestines of poultry in need thereof comprises administering to a poultry bird an effective amount of an interleukin-10 peptide or an isolated antibody that specifically binds an interleukin-10 peptide, wherein administering is within 1 to 4 weeks of harvest of the poultry.

In another aspect, a poultry finishing feed composition comprises a basal poultry finishing feed composition, an amount of an interleukin-10 peptide or an isolated antibody that specifically binds an interleukin-10 peptide, and no added antibiotics, wherein the basal poultry finishing feed composition is suitable for feeding during the final 1 to 4 weeks prior to slaughter.

The above-described and other features will be appreciated and understood by those skilled in the art from the following detailed description, drawings, and appended claims.

DETAILED DESCRIPTION

Described herein are methods of reducing *Salmonella* in the intestines of animals, particularly poultry. Certain interleukin-10 (IL-10) peptides and anti-IL-10 peptide antibodies have been described as useful in the treatment of Coccidiosis, a protozoal infection, in animals such as poultry. The principal downside to Coccidiosis is the growth suppression and other disease effects in the birds as Coccidia is generally not transferrable to humans consuming poultry products. Because young birds are more susceptible to Coccidiosis than more mature birds, Coccidiosis is generally treated by providing anti-Coccidial agents in starter feeds. In commercial chicken production, for example, starter feeds are generally used only in the first 3 weeks of a chick's life due to the early susceptibility to Coccidiosis, the expense of feed containing additives, and concerns about carry-over of agents into produced meat. In turkeys, starter feeds may be used for 6-8 weeks after hatch. In contrast to Coccidia, infection with *Salmonella* bacteria often does not produce symptoms in the infected poultry, but is a serious problem when passed to humans through consumption of poultry products. An additive that can reduce *Salmonella* in the intestines of poultry when used in the final 1 to 4 weeks prior to harvest would greatly reduce the passage of *Salmonella* from poultry to humans through consumption of poultry meat. It was thus found by the present inventors that IL-10 peptides and anti-IL-10 peptide antibodies are also effective against *Salmonella* and represent a new strategy to prevent transmission of *Salmonella* to humans.

In one aspect, described herein is a method of reducing *Salmonella* in the intestines of poultry in need thereof comprising administering to a poultry bird an effective amount of an interleukin-10 peptide or an isolated antibody that specifically binds an interleukin-10 peptide, wherein administering is within 1 to 4 weeks of harvest of the poultry. As used herein, poultry means domesticated fowl raised for meat or eggs. In general, broiler chickens are harvested at 5 to 8 weeks after hatch, thus the interleukin-10 peptide or an isolated antibody that specifically binds an interleukin-10 peptide would be administered at weeks 3, 4, 5, 6, 7 and/or 8 after hatch. Turkeys are harvested between weeks 10-22 after hatch, thus the interleukin-10 peptide or an isolated antibody that specifically binds an interleukin-10 peptide would be administered at weeks 8, 9, 10, 11, 12, 13, 14, 15, 16, 17, 18, 19, 20, 21 and/or 22 after hatch.

The IL-10 peptides and isolated antibodies that specifically bind to IL-10 peptides described herein reduce the *Salmonella* burden in chickens. Specifically, isolated antibodies that specifically bind to IL-10 peptides reduced the *Salmonella* burden in the ceca of chickens challenged with *Salmonella enteritidis*. In one aspect, the poultry to be treated is a *Salmonella*-tolerant bird, meaning that the bird is asymptomatic for Salmonellosis.

As used herein, the term "peptide" includes the peptide as well as pharmaceutically acceptable salts of the peptide. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids.

As used herein, the term "antibody", or "immunoglobulin", encompasses naturally occurring antibodies, such as polyclonal and monoclonal antibodies, as well as artificial or synthetic antibodies or genetically engineered forms of antibodies, including single chain antibodies, chimeric, and bifunctional antibodies, as well as fragments thereof.

The term "isolated antibody" as used herein, refers to an antibody that is substantially free of other naturally associated molecules, or substantially free of antibodies having different antigenic specificities.

The IL-10 peptide of the present disclosure includes the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof (see Table 1). In particularly suitable embodiments, the IL-10 peptide has an amino acid sequence of SEQ ID NO: 1, SEQ ID NO: 2, SEQ ID NO: 3, SEQ ID NO: 4, and/or SEQ ID NO: 5.

TABLE 1

Sequence ID NO. and Corresponding Amino Acid Sequence.

| SEQ ID NO: | AMINO ACID SEQUENCE | Organism |
|---|---|---|
| SEQ ID NO: 1 | DDELNIQL | Chicken, quail, turkey |
| SEQ ID NO: 2 | VLPRAMQT | chicken |
| SEQ ID NO: 3 | VLPRAMKT | Quail and turkey |
| SEQ ID NO: 4 | EKMDENGI | Chicken, quail, turkey |

TABLE 1-continued

Sequence ID NO. and Corresponding Amino Acid Sequence.

| SEQ ID NO: | AMINO ACID SEQUENCE | Organism |
|---|---|---|
| SEQ ID NO: 5 | EPTCLHFS | Chicken, quail, turkey |
| SEQ ID NO: 6 | DQMGDLL | pig |
| SEQ ID NO: 7 | DQLHSLL | cow |
| SEQ ID NO: 8 | VMPKAESD | pig |
| SEQ ID NO: 9 | VMPQAENH | Cow/sheep |
| SEQ ID NO: 10 | SKLQERGV | pig |
| SEQ ID NO: 11 | SELQERGV | cow |
| SEQ ID NO: 12 | ENSCIHFP | pig |
| SEQ ID NO: 13 | DSSCIHLP | cow |
| SEQ ID NO: 14 | DQLNSML | sheep |
| SEQ ID NO: 15 | NMLQERGV | sheep |
| SEQ ID NO: 16 | DSSCTHFP | sheep |
| SEQ ID NO: 17 | DDLEIGL | fish |
| SEQ ID NO: 18 | VLPTAIADMTEE | fish |
| SEQ ID NO: 19 | TQMEGKGP | fish |
| SEQ ID NO: 20 | NQCCRFV | fish |

SEQ ID NO: 1, SEQ ID NO: 2, SEQ ID NO: 3, SEQ ID NO: 4, and/or SEQ ID NO: 5 are amino acid sequences corresponding to peptides of the IL-10 cytokine in poultry, such as chickens, quail, and turkeys. The IL-10 peptides of the present disclosure should reduce the *Salmonella* burden in the ceca of chickens challenged with *Salmonella enteritidis* by interfering with IL-10 signaling and *Salmonella* tolerance.

The present disclosure further includes antibodies that specifically bind to the IL-10 peptides (also referred to herein as "anti-IL-10 antibody"). These antibodies have surprisingly been found to reduce the *Salmonella* burden in the ceca of chickens challenged with *Salmonella enteritidis* when isolated and administered thereto. The antibodies of the present disclosure specifically bind to IL-10 peptides including the amino acid sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO:14, SEQ ID NO: 15, SEQ ID NO: 16, SEQ ID NO: 17, SEQ ID NO: 18, SEQ ID NO:19, SEQ ID NO: 20, and combinations thereof. In some embodiments, the isolated antibodies specifically bind to IL-10 peptides having an amino acid sequence of SEQ ID NO: 1, SEQ ID NO: 2, SEQ ID NO: 3, SEQ ID NO: 4, and/or SEQ ID NO: 5. In other embodiments, the isolated antibodies bind SEQ ID NO: 2, SEQ ID NO: 3, or both.

The present disclosure is further directed to generating antibodies that specifically bind to the IL-10 peptides. In one embodiment, an antibody is generated by administering the IL-10 peptides described above to an animal. Suitable animals to administer the IL-10 peptides for generating the antibodies include, for example, poultry. Exemplary poultry include chickens, turkeys, ducks, quail, and pheasant. Specific poultry include turkeys and chickens. Additional animals include livestock animals such as cows, pigs, sheep, and fish.

Exemplary methods for administering the IL-10 peptides to the animal include injection and oral administration. Injection and oral administration optionally include use of an adjuvant such as, for example, Freund's Complete adjuvant and Cholera toxin. Administration optionally further includes conjugation of the IL-10 peptide to a carrier protein such as, for example, bovine gamma globulin or keyhole limpet hemocyanin.

In one embodiment, antibodies to the IL-10 peptides are generated by an animal (referred to herein as the "producer animal"). When the animal is an avian animal, as know by those skilled in the art, the antibodies generated are passed to the egg, and may specifically be concentrated in the egg yolk of the avian producer animal. Alternatively, antibodies of the present disclosure may be isolated from the animal itself such as from serum.

In one embodiment, the antibody is an avian egg yolk antibody. Egg yolks derived from a laying hen are inexpensive, convenient and can be safer to handle as compared to the hyperimmunized mammalian sera. Also, egg yolk antibodies are able to stand up to the scrutiny under modern animal protection regulations Immunoglobulin Y (IgY) is an avian immunoglobulin.

To produce avian egg yolk antibodies, the IL-10 peptides are injected into laying fowl, such as hens, preferably at various intervals, to induce an immune response. The hens may be injected intramuscularly or sub-cutaneously. The specific mode of injection is not essential. It is well known that the IgY antibodies produced by the hens in response to such an immune challenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying methods, and the resulting dried powder may be encapsulated or otherwise used in oral dosage forms.

Alternatively, a procedure of partial purification or fractionation may be carried out to remove the majority of the non-aqueous bio-molecules and granules and optionally the majority of other proteins in the egg yolk. Exemplary purification techniques include the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, pH is about 5-7. Desirably, the temperature in this step is within about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include, but are not limited to, NaCl, $Na_2SO_4$, $(NH_4)_2SO_4$, KCl, $CaCl_2$, and $MgSO_4$. Specific salts include $Na_2SO_4$ and $(NH_4)_2SO_4$. The salt concentration for precipitating antibodies depends on the type of the salt. In one embodiment, the salt is present in an amount of higher than 15% and lower than 35% by weight, specifically between 20% and 30% by weight of the salt, on the basis of the final volume of the yolk supernatant.

Alternatively, the antibodies may be purified or isolated using any conventional technique such as by immunoaffinity purification.

In one embodiment, egg yolk antibodies are prepared by the following method. Laying hens are inoculated with IL-10 peptide. Optionally, an adjuvant is administered in conjunction with the IL-10 peptide to enhance the immunization. An adjuvant useful for this purpose is a water-in-oil emulsion adjuvant such as complete Freund's adjuvant. The IL-10 peptide causes the hens to produce anti-IL-10 antibodies which are passively transferred into the egg yolk of eggs laid by the hens.

Egg yolks or whole eggs containing the anti-IL-10 antibody can be collected and homogenized to form an emulsion. The resulting emulsion can be dried to form a powder containing the anti-IL-10 antibody. This powder can then be formulated in a manner appropriate to the administration route and then administered to the desired animals using methods known in the art. The preparation is preferably administered orally, such as in an oral dosage form or in a supplement to the animal's diet.

The antibodies that specifically bind to IL-10 peptides may be isolated and purified from animal serum or egg using a suitable method known in the art. Such methods include affinity chromatography, as well as other suitable methods for antibody isolation and purification known in the art and described in U.S. Pat. No. 6,608,172 and De Meulenaer et al., "Isolation and Purification of Chicken Egg Yolk Immunoglobulins: A Review," Food and Agricultural Immunology, Vol. 13(4), 2001, hereby incorporated by reference to the extent that they are consistent herewith. In one particularly suitable embodiment, the production animal is an avian animal such as a chicken, turkey, duck, or quail, and the antibody is isolated from the egg yolk of the egg of the avian animal.

In one embodiment, the egg yolk or serum including the antibodies are further dried to form a powder including the antibodies. The whole egg, egg yolk or parts of the egg may be spray dried. Serum may be separated from whole blood according to methods known by those skilled in the art. Spray drying of egg and serum may be performed using known spray drying methods and commercially available spray drying equipment. Dry egg and serum powders may also be prepared by lyophilization. The dried egg, egg yolk or serum powder may then be introduced into animal feeds as a feed additive to transfer antibodies to an animal.

The present disclosure is further generally directed to animal feed additives including the IL-10 peptides, or isolated antibodies which specifically bind to IL-10 peptides.

As used herein, the term "feed" broadly refers to a material, liquid or solid, that is used for nourishing an animal, and for sustaining normal or accelerated growth of an animal including newborns or young and developing animals. The term includes a compound, preparation, mixture, or composition suitable for intake by an animal. Specifically, the feed is suitable for poultry such as quail, ducks, turkeys, and chickens. A feed composition comprises a basal food composition and one or more feed additives. The term "basal food composition" refers to a food composition combinable with additives such as the peptides and antibodies described herein. Basal animal food compositions may include components such as proteins, grains, flavor compositions, vitamins, minerals, preservatives, and the like. Basal food compositions can be suitable for ingestion by a target animal. The term "feed additive" as used herein refers to components included in small quantities for the purpose of fortifying basic feed with nutrients, stimulants, medicine, or to promote feed intake or alter metabolism. Feed additives include pre-mixes of biological compositions, or in the present disclosure, pre-mixes of IL-10 peptide or isolated antibody that specifically binds to IL-10 peptide.

In one embodiment, the present disclosure includes an animal feed additive including IL-10 peptides including the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. Particularly, the feed additive may include IL-10 peptides having an amino acid sequence of SEQ ID NO: 1, SEQ ID NO: 2, SEQ ID NO: 3, SEQ ID NO: 4, and/or SEQ ID NO: 5.

In another embodiment, the present disclosure includes an animal feed additive including isolated antibodies that specifically bind to the IL-10 peptide including the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. In particularly suitable embodiments, the feed additive includes isolated antibodies that specifically bind to IL-10 peptides having the amino acid sequence of SEQ ID NO: 1, SEQ ID NO: 2, SEQ ID NO: 3, SEQ ID NO: 4, and/or SEQ ID NO: 5.

The IL-10 peptides or isolated antibodies which specifically bind to IL-10 peptides may be added to an animal feed as a feed additive or mixed into an animal feed by a method known in the art for mixing feed additives and animal feed. In one embodiment, the IL-10 peptide or isolated antibody which specifically binds to the IL-10 peptide is directly added to the animal feed or mixed with the animal feed just prior to feeding the animal. In another embodiment, since feeds may be pelleted or extruded, the IL-10 peptide or isolated antibody which specifically binds to the IL-10 peptide may be coated on the surface of feed (pellet) after the feed has been pelleted or extruded (post pelleted application) in order to maintain functional properties of the IL-10 peptide or isolated antibody which specifically binds to the IL-10 peptide. The addition of the IL-10 peptide or isolated antibody which specifically binds to the IL-10 peptide post pelleting can be aided by mixing the IL-10 peptide or isolated antibody which specifically binds to the IL-10 peptide in water, oil, or another suitable carrier and spraying it on the pellets as they exit the pellet die.

The amount of the IL-10 peptide or isolated antibody that specifically binds to IL-10 peptide added and/or mixed with the animal feed depends on the feeding regimen and the type of feed for the animal, and may be determined by those skilled in the art. Typically, the amounts of IL-10 peptides and/or isolated antibodies to IL-10 peptide to be used in an animal feed are summarized in Table 2 below. Antibody prepared using other sources may be calculated as equivalents using Table 2.

TABLE 2

Dose of Anti-IL-10 Antibody in Animal Feed (mg/Kg diet) prepared using egg yolk antibody.

| Source | Low Dose | High Dose |
|---|---|---|
| Affinity purified anti-peptide | 0.0015 | 0.5 |
| Anti-peptide IgY | 0.015 | 50 |
| Dry Immune Yolk | 0.8 | 4000 |
| Dried Immune Whole Egg | 1.5 | 7500 |

The doses shown are based on the amount of epitope specific antibody in total IgY (1 to 10%), the amount of IgY in egg (5-10 mg/Kg of feed), antibody losses due to drying storage and gastrointestinal degradation.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

Specifically, the animal feed including the feed additive of either IL-10 peptide or isolated antibody is a feed for avian species such as quail, ducks, turkeys, and chickens.

In a specific embodiment, the animal feed is a finishing feed, that is, a feed composition used for poultry for consumption that is generally used in the last 1 to 4 weeks prior to slaughter to bring the poultry to market weight. Finishing feeds do not contain antibiotics and other additives that might be transferred to the meat produced upon slaughter. Finishing feeds can be distinguished from starter feeds which contain, for example, antibiotics and anti-coccidial agents which are crucial to prevent disease prior to the development of immune defenses in the young animal. Finishing feeds can also be referred to as withdraw feeds.

In one aspect, poultry finishing feed composition comprises a basal poultry finishing feed composition, an amount of an interleukin-10 peptide or an isolated antibody that specifically binds an interleukin-10 peptide, and no added antibiotics, wherein the basal poultry finishing feed composition is suitable for feeding during the final 1 to 4 weeks prior to slaughter. The interleukin-10 peptides includes SEQ IDs: 1-5. In specific embodiments, the peptide or isolated antibody is present in the poultry feed composition in an amount of 0.15 mg/kg of animal feed to 100 mg/kg of poultry feed.

The methods of the present disclosure are generally directed to methods for treating gastrointestinal *Salmonella* infection in an animal, or in an animal with a status of convalescence carriers of pathogen. In one embodiment, the methods involve injecting or orally administering an IL-10 peptide to an animal, thereby producing antibodies within the animal that specifically bind to the IL-10 peptide. IL-10 cytokine production is associated with down regulation of inflammation, and the IL-10 cytokine functions as an essential immunoregulator of the intestinal tract. The antibody to IL-10 peptide prevents the IL-10 cytokine from down regulating the immune system, thereby allowing the immune system to eliminate the pathogen.

In some embodiments, the methods involve injecting or orally administered an antibody to the IL-10 peptide to an animal. The term "animal", as used herein to describe animals administered an IL-10 peptide or isolated antibody to the IL-10 peptide in accordance with the present disclosure, includes poultry such as quail, ducks, turkeys, pheasants, and chickens.

In one aspect, the present disclosure is directed to methods for preventing the transfer of human pathogens from poultry that are infected or incubatory or convalescent carriers of human pathogens to the human consumer of poultry products, or at risk of being infected or incubatory or convalescent carriers of pathogens by administering isolated antibodies that specifically bind to IL-10 peptides including the amino acid sequences selected of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and combinations thereof. For example, the methods may include administering isolated antibodies that specifically bind to IL-10 peptides having the amino acid sequence of SEQ ID NO: 1, SEQ ID NO: 2, SEQ ID NO: 3, SEQ ID NO: 4, and/or SEQ ID NO: 5. As used herein "at risk of" refers to having little resistance to a certain condition or disease (i.e., bacterial infection), including being genetically predisposed, having a family history of, and/or having symptoms of the condition or disease, or in a state of being a incubatory or convalescent carrier of pathogens and being exposed to other animals that have been exposed to or have the condition, disease or carrier status.

In an aspect, described herein is a method of reducing *Salmonella* in the intestines of a mammal or fish in need thereof comprising administering an effective amount of an interleukin-10 peptide or an isolated antibody that specifically binds an interleukin-10 peptide, wherein administering is within 1 to 4 weeks of harvest of the mammal or fish. When the animal is a mammal, exemplary IL-10 peptides are SEQ ID NOs: 6-16. When the animal is a fish, exemplary IL-10 peptides are SEQ ID NOs: 17-20.

The invention is further illustrated by the following non-limiting examples.

EXAMPLES

Example 1: Detection of Antibody Production

In this Example, the concentration of anti-IL-10 antibody production contained within the egg yolk of IL-10 peptide-administered producer hens was determined by using Enzyme-linked immunosorbent assay (ELISA) techniques.

Specifically, each of four IL-10 peptides selected from the group consisting of IL-10 Peptide #1 (SEQ ID NO: 1), IL-10 Peptide #2 (SEQ ID NO: 2), IL-10 Peptide #3 (SEQ ID NO: 4), and IL-10 Peptide #4 (SEQ ID NO: 5) was conjugated to hen ovalbumin (OVA, Sigma, St. Louis, Mo.) for ELISA using glutaraldehyde procedure. A 96-well NUNC® immunosorbent F-series microplate (Sigma, St. Louis, Mo.) was coated with 100 µg/plate of peptide-specific OVA conjugate in sodium carbonate coating buffer having a pH of 9.6. The plate was allowed to coat overnight (100 µl/well) at 4° C. Dry egg yolk samples containing antibody to IL-10 Peptide #1, #2, #3, or #4 were diluted 1:10 in acidic PBS having a pH of 4 and allowed to incubate overnight at 4° C. After overnight incubation, the antibody was extracted using centrifugation and used as a source of antibody to determine specificity for the peptide conjugated to the IL-10 peptide. The plate coated with OVA-peptide conjugate was washed 6 times with PBS/0.5% TWEEN® (polysorbate 20, polyoxyethylene (20) sorbitan monolaurate) solution, blocked with non-protein blocking buffer (200 µl/well, Pierce Scientific, Rockford, Ill.), and allowed to incubate at room temperature for at least 1 hour. The plate was washed 6 times and then samples of either adjuvant only injected control or egg antibody (isolated as described above) were added at a concentration of 100 µl/well in duplicate at 10× serial dilutions starting at 1:1000. Primary antibodies were incubated for 1 hour, the plate was washed 6 times, and then secondary antibody (HRP-conjugated goat anti-chicken antibody, Bethyl Labs, Montgomery, Tex.) was diluted in blocking buffer 1:5000 and added at a concentration of 100 µl/well. Secondary antibody was incubated for 30 minutes, the plate was washed 6 times, and then substrate solution containing 19.74 ml 0.05M sodium acetate, 100 µl 20 mg/mL 3,3',5,5' Tetramethyl Benzidine (TMB), 128 µl 0.5M $H_2O_2$ was added at a concentration of 125 µl/well and allowed to incubate until sufficient color development during the linear phase of development (blue color indicates primary antibody presence). A stop solution (0.5M sulfuric acid) was added to produce a yellow stable color and the plate was read at 450 nm on a BIOTEK™ EL800 plate reader. Duplicate optical densities were averaged and blocking buffer background was subtracted to produce a final optical density. The optical density of antibody to IL-10 peptides #1-4 and FCA control were compared to determine specificity and dose level used in the final chick experiment (see Table 3).

TABLE 3

Optical Densities of Anti-IL-10 Peptides.

| Dilution | IL-10 #1 | IL-10 #2 | IL-10 #3 | IL-10 #4 |
| --- | --- | --- | --- | --- |
| 10 | 1.0585 | 0.935 | 0.968 | 0.8822 |
| 100 | 1.049 | 1.006 | 0.973 | 0.9 |
| 1000 | 0.9705 | 1.033 | 1.001 | 0.678 |
| 10000 | 0.4795 | 0.6775 | 0.593 | 0.224 |
| 100000 | 0.075 | 0.129 | 0.115 | 0.059 |
| 1000000 | 0.028 | 0.03 | 0.037 | 0.03 |
| 10000000 | 0.059 | 0.016 | 0.027 | 0.028 |
| 100000000 | 0.022 | 0.0055 | 0.0181 | 0.033 |
| FCA | 0.562 | | 0.499 | 0.60 |

Example 2: Anti-IL-10 Antibody Feed Study in Chickens

This study was performed to determine whether an anti-IL-10 antibody can decrease *Salmonella* carrier status in poultry, specifically chickens. Chicks were challenged with *Salmonella enteritidis* ($10^6$ per chick on day 4 or 5 post-hatch) or not challenged. This experimental protocol allows chick to become recovered carriers and thus incubatory or convalescent carriers of pathogens for humans. The antibody used was an egg yolk antibody to peptide SEQ ID NO: 2. Control antibodies were made by injecting chickens with adjuvant only (FCA antibody or isotype adjuvant control antibody). Fourteen treatments were performed:
 1. normal diet, no challenge (60 chicks/pen)
 2. normal diet, SE challenge (60 chicks/pen)
 3. Control ab diet (0.341 g/Kg), no challenge (50 chicks/pen)
 4. Control ab diet (1.705 g/Kg), no challenge (50 chicks/pen)
 5. Control ab diet (3.41 g/Kg), no challenge (50 chicks/pen)
 6. Control ab diet (0.341 g/Kg), SE challenge (50 chicks/pen)
 7. Control ab diet (1.705 g/Kg), SE challenge (50 chicks/pen)
 8. Control ab diet (0.341 g/Kg), SE challenge (50 chicks/pen)
 9. IL-10 ab diet (0.341 g/Kg), no challenge (50 chicks/pen)
 10. IL-10 ab diet (1.705 g/Kg), no challenge (50 chicks/pen)
 11. IL-10 ab diet (3.41 g/Kg), no challenge (50 chicks/pen)
 12. IL-10 ab diet (0.341 g/Kg), SE challenge (50 chicks/pen)
 13. IL-10 ab diet (1.705 g/Kg), SE challenge (50 chicks/pen)
 14. IL-10 ab diet (3.41 g/Kg), SE challenge (50 chicks/pen)

Figure 1:
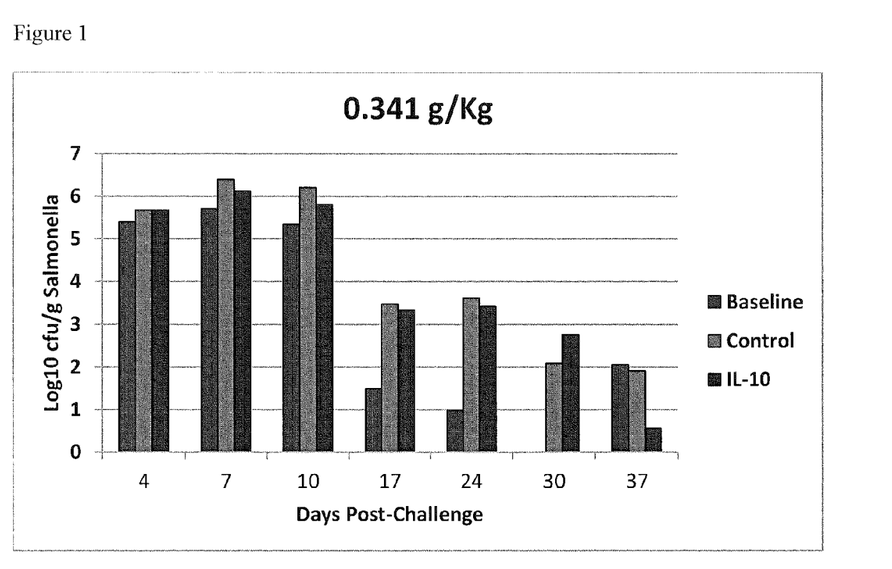
FIG. 1 shows the *Salmonella* counts vs. days post challenge at 0.341 g of antibody/kg of feed.
Figure 2:
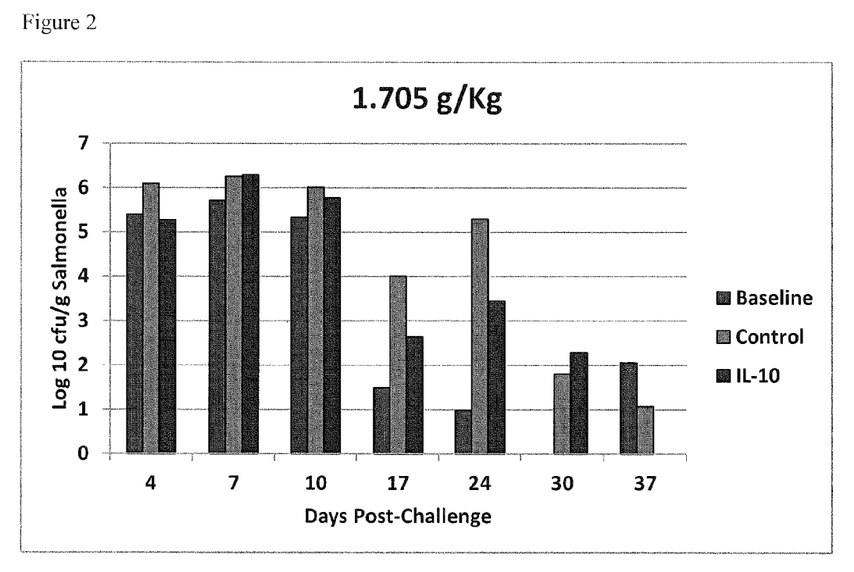
FIG. 2 shows the *Salmonella* counts vs. days post challenge at 1.705 g of antibody/kg of feed.
Figure 3:
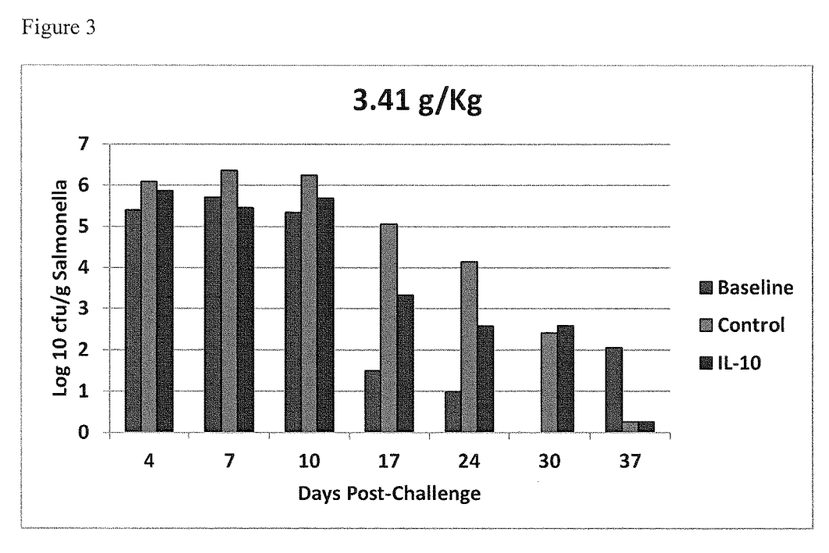
FIG. 3 shows the *Salmonella* counts vs. days post challenge at 3.41 g of antibody/kg of feed.

Chicks were placed on their respective diet immediately post-hatch. At baseline (2 days post-hatch) and each timepoint (7, 11, 14, 18, 21, 30, 35 and 42 days post-hatch), five birds were sacrificed. The samples collected include: Blood, cecal content for *Salmonella* cfu; cecal for enrichment; tissues from ceca, liver and muscle; intestine; and cecal tonsils FIG. 1 shows the cecal *Salmonella* counts vs. days post challenge at 0.341 g of antibody/kg of feed. FIG. 2 shows the cecal *Salmonella* counts vs. days post challenge at 1.705 g of antibody/kg of feed. FIG. 3 shows the cecal *Salmonella* counts vs. days post challenge at 3.41 g of antibody/kg of feed. In chicks not infected with *Salmonella*, *Salmonella* was not isolated (not shown). Shown in FIGS. 1-3 is the colony forming units (CFU) per gram of cecum contents. The first ten days post infection, there was no difference in the CFU between treatment groups. All chicks regardless of treatment had between 5 and 7 Log 10 *Salmonella* per gram of cecal matter. This finding showed that the anti-IL-10 antibody was not effective at preventing infection. Beginning on day 17 post-infection, the number of *Salmonella* per gram of cecal matter decreased, such that by day 37 the chicks not provided with either control or anti-IL-10 antibody stabilized at approximately 2 Log 10 CFU/gram cecal content, a level of bacteria that would be consistent with an incubatory or convalescent carrier status for *Salmonella*. The finding of no *Salmonella* in the ceca of control birds (n=5) at day 30 was a sampling error, since at day 37 it was clear that control chicks still had cecal *Salmonella*. For detecting *Salmonella*, a level of *Salmonella* of 1 Log 10 or greater is considered incubatory or convalescent carrier of *Salmonella*. None of the chicks fed anti-IL-10 had a carrier status by day 37. Also at day 37, 20% (1/5) of the birds not fed either control nor anti-IL-10 antibody and 20% (3/15) of chicks fed control antibody had a greater than 1 Log 10 *Salmonella*, whereas 0/15 of the anti-IL-10 chicks had *Salmonella*. Hence the use of anti-IL-10 antibodies at all doses studied eliminated an incubatory or convalescent carrier status for the chicks, where as 20% of those fed the control antibody or no antibody continued to be incubatory or convalescent carrier of *Salmonella*. Another objective estimate of the effects of the anti-IL-10 antibody is that the anti-IL-10 antibody reduced the amount of *Salmonella* in the ceca of chickens by at least 100-fold at all concentrations tested. These data suggest that the amount of antibody may be lowered from the lowest level of 0.341 g of antibody/kg of feed (0.341 g antibody/Kg of feed is equivalent to 0.7 pounds of antibody-containing yolk powder/ton of feed).

Example 3: Anti-IL-10 Antibody Feed Study in Turkeys

The USDA Food Safety and Inspection Service has decreased the tolerance for naturally abundant *Salmonella* species on turkey products. A study will be conducted to determine if the number of positive tests following USDA guidelines can be decreased by the use of anti-IL-10 antibody in the withdraw diet of turkeys. Turkey Toms 14-18 weeks of age are placed either on a withdraw diet with no added anti-IL-10 antibody, or a withdraw diet supplemented with 3.1 Kg IL-10 antibody in a dried egg yolk carrier per ton of feed. Turkeys are fed the two diets for two weeks, turkeys are slaughtered, and whole turkeys and their products are tested using the USDA guidelines for the present of *Salmonella* species. The incidence of *Salmonella* on turkey carcasses can be 2% in those turkeys fed a control diet, and should be lower in those turkeys fed a diet containing anti-IL-10 antibody. Ground turkey meat will also be analyzed. Control fed turkeys can have 11% or more *Salmonella* positive samples, while those turkeys fed a diet containing anti-IL-10 antibody should have fewer than 11% *Salmonella* positive samples.

The use of the terms "a" and "an" and "the" and similar referents (especially in the context of the following claims)

are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of reducing *Salmonella* in the intestines of poultry in need thereof, comprising
    administering to a poultry bird an effective amount of an isolated antibody that specifically binds an interleukin-10 peptide,
    wherein administering is within 1 to 4 weeks of harvest of the poultry,
    wherein the interleukin-10 peptide is SEQ ID NO: 1, SEQ ID NO: 2, SEQ ID NO: 3, SEQ ID NO: 4, SEQ ID NO: 5.

2. The method of claim 1, wherein the poultry bird is a *Salmonella* incubatory or convalescent carrier.

3. The method of claim 1, wherein the isolated antibody specifically binds SEQ ID NO: 2, or SEQ ID NO: 3.

4. The method of claim 1, wherein the poultry is a chicken, a turkey, a duck, a quail, or a pheasant.

5. The method of claim 1, wherein the poultry is a chicken, and wherein the isolated antibody that specifically binds the interleukin-10 peptide is administered at weeks 3, 4, 5, 6, 7, and/or 8 after hatch.

6. The method of claim 1, wherein the poultry is a turkey, and wherein the isolated antibody that specifically binds the interleukin-10 peptide is administered at weeks 8, 9, 10, 11, 12, 13, 14, 15, 16, 17, 18, 19, 20, 21 and/or 22 after hatch.

7. The method of claim 1, wherein the isolated antibody is administered by injection or oral administration.

8. The method of claim 1, wherein the isolated antibody is in the form of an avian egg yolk antibody.

9. The method of claim 8, wherein the isolated antibody specifically binds SEQ ID NO: 2, or SEQ ID NO: 3.

10. The method of claim 1, wherein the isolated antibody is administered in the form of a poultry feed composition.

11. The method of claim 10, wherein the poultry feed composition is a finishing feed comprising no added antibiotics.

12. The method of claim 10, wherein the isolated antibody is present in the poultry feed composition in an amount of 0.15 mg/kg of animal feed to 100 mg/kg of poultry feed.

* * * * *